United States Patent [19]

Buenger et al.

[11] Patent Number: 5,334,176

[45] Date of Patent: Aug. 2, 1994

[54] ABSORBENT CORE FOR USE IN CATAMENIAL PRODUCTS

[75] Inventors: Daniel E. Buenger; James C. Horney, both of Cincinnati; John L. Hammons, Hamilton, all of Ohio

[73] Assignee: The Procter & Gamble Company, Cincinnati, Ohio

[21] Appl. No.: 734,405

[22] Filed: Jul. 23, 1991

[51] Int. Cl.$^5$ .................. A61F 13/15; A61F 13/20
[52] U.S. Cl. ........................... 604/367; 604/358; 604/374; 604/384
[58] Field of Search ............ 604/367, 374, 378, 384, 604/358; 162/9, 23, 100, 111, 129–131; 428/369, 373, 397

[56] References Cited

U.S. PATENT DOCUMENTS

| | | | |
|---|---|---|---|
| 3,663,348 | 5/1972 | Liloila et al. | 604/374 |
| 3,700,544 | 10/1972 | Matsui | 428/373 |
| 3,726,277 | 4/1973 | Hirschman | 604/904 |
| 4,085,754 | 4/1978 | Ness et al. | 604/390 |
| 4,223,677 | 9/1980 | Anderson | 604/378 |
| 4,324,247 | 4/1982 | Aziz | 604/378 |
| 4,578,070 | 3/1986 | Holtman | 604/378 |
| 4,822,543 | 4/1989 | Iizuka et al. | 264/521 |
| 4,888,093 | 12/1989 | Dean et al. | 162/157.6 |
| 4,889,595 | 12/1989 | Herron et al. | 162/157.6 |
| 4,889,596 | 12/1989 | Schoggen et al. | 162/157.6 |
| 4,889,597 | 12/1989 | Bourbon et al. | 162/157.6 |
| 4,898,642 | 2/1990 | Moore et al. | 162/157.6 |
| 4,935,022 | 6/1990 | Lash et al. | 604/368 |
| 5,057,368 | 10/1991 | Largman et al. | 428/397 |
| 5,147,345 | 9/1992 | Young et al. | 604/367 |

FOREIGN PATENT DOCUMENTS

| | | |
|---|---|---|
| 193309A1 | 9/1986 | European Pat. Off. . |
| 0391814A2 | 10/1990 | European Pat. Off. . |
| 427316A2 | 5/1991 | European Pat. Off. . |
| 427317A2 | 5/1991 | European Pat. Off. . |
| 429112A2 | 5/1991 | European Pat. Off. . |
| WO89/10446 | 2/1989 | PCT Int'l Appl. . |

*Primary Examiner*—Randall L. Green
*Assistant Examiner*—P. Zuttarelli
*Attorney, Agent, or Firm*—Kevin C. Johnson; Jerry J. Yetter

[57] ABSTRACT

Curled, twisted cellulosic fibers are reduced in size by mechanical means, i.e., by refining. The refined fibers are formed into sheets which are used as an absorbent layer in diapers, bandages and, especially, in sanitary napkins. In one mode, the refined fibers can be used to provide shaped sanitary devices. In an optional mode, fibers having intra-fiber capillary channels can be used to direct fluids into absorbent sheets comprising the refined, curled cellulosic fibers.

20 Claims, 6 Drawing Sheets

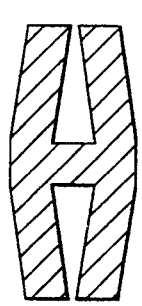 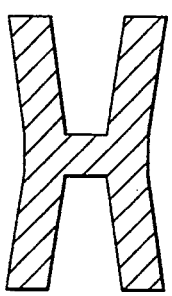 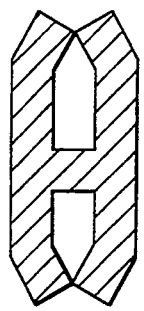
Fig. 6A     Fig. 6B     Fig. 6C
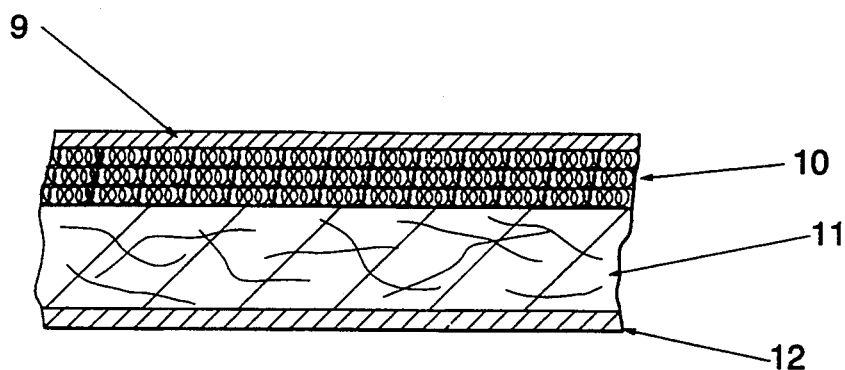
Fig. 7
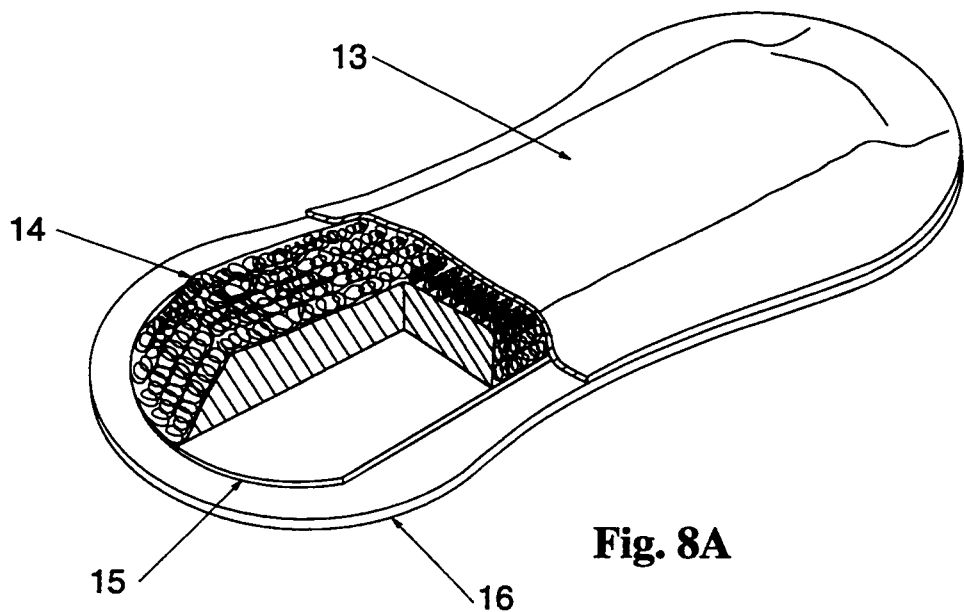
Fig. 8A

ABSORBENT CORE FOR USE IN CATAMENIAL PRODUCTS

TECHNICAL FIELD

The present invention relates to fibrous cores which are used to provide absorbent capacity in catamenial products, especially sanitary napkins and pantiliners. The absorbent fibrous cores herein are particularly useful under circumstances where the use of absorbent gelling materials and/or latex binders is not desirable.

BACKGROUND OF THE INVENTION

A wide variety of structures for use in catamenial articles such as sanitary napkins and pantiliners are well-known in the literature. In general, such articles comprise a fluid-permeable topsheet, an absorbent core, and a fluid-impermeable backsheet. Typically, the absorbent core of such articles comprises cellulosic fibers of one type or another. Northern Softwood Kraft, Southern Softwood Kraft, chemi-thermomechanical pulps, and the like, have all been suggested for use as absorbent materials in catamenials. Modern catamenials often contain absorbent gelling materials, such as polyacrylates and starch-acrylate grafts, to provide additional absorbent capacity.

There is a continuing search for more economical, yet effective, absorbent core materials. Moreover, modern catamenial products, especially sanitary napkins and pantiliners, are now becoming available in ultra-thin forms. Such ultra-thin forms provide additional comfort to the wearer, but require especially effective absorbent cores in order to provide the desired absorbency and protection from failure, in-use. In the main, current ultra-thin cores employ a mixture of cellulose fibers and absorbent gelling materials, as noted above.

However, there are drawbacks even to the modern ultra-thin cellulose/absorbent gelling material cores. For example, the use of absorbent gelling materials in manufacturing processes can be problematic, inasmuch as such materials can be dusty and difficult to handle. Moreover, absorbent gelling materials can be expensive. Indeed, absorbent gelling materials were primarily developed to absorb low viscosity fluids such as urine, e.g., in infant diapers, and some types of absorbent gelling materials are not optimally useful with more viscous liquids such as menses. Finally, the formulation of ultra-thin absorbent pads from ordinary cellulosic fibers and absorbent gelling materials often requires the use of latex binders, which can amount to as much as 20% by weight of the total cellulosic fibers in the core. Such binders are necessary to provide strength and cohesiveness to the core during manufacturing operations and also under in-use conditions after the cores become moistened by body fluids.

Until now, the development of absorbent core materials for use in sanitary napkins and pantiliners has relied to a considerable extent on learnings associated with the manufacture of disposable infant diapers. The absorbent gelling materials in both types of products are quite similar. The cellulosic fibers used in both types of products are very similar. Yet, it will be appreciated that the nature of the fluids being absorbed in diapers vs. catamenials is substantially different. Moreover, diapers have much higher volume requirements and a much greater need for moving such higher volumes of liquids through larger distances and heights in the absorbent core than do catamenial products. Thus, having given due consideration to these factors, it has now been determined that cellulosic materials of the type described hereinafter can very admirably serve as the absorbent core in sanitary napkins and pantiliners.

Accordingly, it is an object of the present invention to provide sanitary napkins and pantiliners having improved absorbent cores. While the absorbent cores provided in this invention can optionally contain absorbent gelling materials, it is a further object herein to provide absorbent cores which function sufficiently well, even when ultra-thin, that absorbent gelling materials are not required. It is a further object herein to provide absorbent cores which have high capillarity in conjunction with high permeability, as well as the ability to hold fluids tenaciously. It is a further object herein to provide catamenial articles whose absorbent cores do not require latex binder. These and other objects are secured by the present invention, as will be seen hereinafter.

BACKGROUND ART

The preparation of curled, chemically crosslinked cellulosic fibers, and their use in various absorbent articles is described in one or more of the following United States patents and patent applications: U.S. Pat. No. 4,888,093 issued Dec. 19, 1989; U.S. Pat. No. 4,822,543 issued Apr. 18, 1989; U.S. Pat. No. 4,889,595 issued Dec. 26, 1989; U.S. Pat. Nos. 4,889,597 issued Dec. 26, 1989; 4,889,596 issued Dec. 26, 1989; U.S. Pat. No. 4,898,642 issued Feb. 6, 1990; U.S. Pat. No. 4,935,022 issued Jun. 19, 1990; U.S. application No. 07/596,605 filed Oct. 17, 1990, issued as Canadian 2,028,977-5, May 8, 1991; U.S. application No. 07/596,606 filed Oct. 17, 1990, issued as Canadian 2,029,025-1, May 8, 1991; U.S. application No. 07/596,607 filed Oct. 17, 1990, issued as Finland PA90-5502, May 7, 1991; U.S. application No. 07/625,776 filed Dec. 17, 1990; U.S. application No. 07/625,775 filed Dec. 17, 1990; and U.S. application No. 07/625,774 filed Dec. 17, 1990.

The preparation of other curled cellulosic fibers which can be used herein is disclosed in PCT Patent Specification U.S. 89 01581 filed 14 Apr., 1989, International Publication No. 89/10446 published Feb. 11, 1989 by M. L. Minton.

The foregoing patents, patent applications and any patent subsequently mentioned herein are incorporated herein by reference.

SUMMARY OF THE INVENTION

The present invention encompasses fluid-absorbent (especially vaginal discharge fluids and menses) wet-laid sheets comprising individualized curled cellulosic fibers, said cellulosic fibers being mechanically refined such that at least about 30% of said fibers have an average length which is from about 20% to about 40% of their length when in their original, unrefined state. Preferably, such sheets will have from about 50% to about 90% of their refined fibers at an average length of from about 0.25 mm to about 1.5 mm. More preferably, such sheets will have an average of from about 0.1 g to about 0.15 g of said refined fibers per cubic centimeter of sheet. Most preferably, such sheets will have an average thickness of from about 0.3 mm to about 2.4 min. Such sheets are prepared as disclosed hereinafter, and, after wet-laying, are preferably dried by through-air drying means.

The invention thus provides sanitary napkins or pantiliners comprising a fluid-impermeable backsheet, a fluid-permeable topsheet and an absorbent core interposed between said topsheet and said backsheet, said core comprising the sheet noted above.

In an alternate mode, the invention encompasses absorbent structures comprising a nonwoven scrim onto which is cohesively wet-laid a layer of individualized curled cellulosic fibers, said cellulosic fibers being mechanically refined such that at least about 30% of said fibers have an average length which is from about 20% to about 40% of their length when in their original, unrefined state. Preferably, such structures will have from about 50% to about 90% of their refined fibers at an average length of from about 0.25 mm to about 1.5 mm. More preferably, such structures will have an average of about 0.1 g to about 0.15 g of said refined fibers per cubic centimeter of said wet-laid layer. Most preferably, such structures will have a layer of said refined cellulosic fibers at an average thickness of from about 0.3 mm to about 2.4 mm. Again, such structures, after wet-laying, are preferably dried by through-air drying means.

Thus, the invention also provides a sanitary napkin or pantiliner comprising a fluid-impermeable backsheet, a fluid-permeable topsheet and an absorbent core interposed between said topsheet and said backsheet, said core comprising the absorbent scrim/layer structure noted above.

In yet another embodiment, the invention also encompasses an absorbent structure comprising a fluid-directing scrim, said scrim comprising fibers having external capillary channels, and wherein a layer of individualized curled cellulosic fibers are cohesively wet-laid onto said scrim, said cellulosic fibers being mechanically refined such that at least about 30% of said fibers have an average length which is from about 20% to about 40% of their length when in their original, unrefined state. As above, preferred structures of this type are those wherein from about 50% to about 90% of the refined fibers have an average length of from about 0.25 mm to about 1.5 mm. Preferably, such structures have an average of from about 0.1 g to about 0.15 g of said refined fibers per cubic centimeter of said wet-laid layer. More preferably, said layer of cellulosic fibers has an average thickness of from about 0.3 mm to about 2.4 min. As noted above, such structures, after wet-laying, are preferably dried by through-air drying means.

In a preferred mode, such structures are those wherein at least about 50%, preferably, at least about 80%, of the fibers having capillary channels are positioned such that their capillary channels lie in the machine direction of the structure.

The invention also provides a sanitary napkin or pantiliner comprising a fluid-impermeable backsheet, a fluid-permeable topsheet and an absorbent core interposed between said topsheet and said backsheet, said core comprising the capillary channel scrim/layer structure noted above, said structure being positioned such that the scrim comprising the capillary channel fibers is in close, fluid-transporting contact with said topsheet. In a preferred embodiment, such sanitary napkin or pantiliner is characterized by having said absorbent core with at least about 50% (preferably at least about 80%) of the capillary channel fibers in its scrim positioned such that the capillary channels lie in the machine direction of the sanitary napkin or pantiliner.

The invention thus provides new absorbent and fluid-handling means for absorbent hygiene products when used in sheet or pad form. Basis Weights per ream (3,000 ft.$^2$) typically will range from about 35 pounds at a thickness of about 0.5 mm to about 150 pounds at a thickness of about 2 mm. In an optional mode, the sheets can contain from about 0% to about 25% by weight of cellulosic crill.

The invention also encompasses 3-dimensional shaped catamenial devices of the convex intralabial, concave external, or pessary types, comprising individualized curled cellulosic fibers, said cellulosic fibers being mechanically refined such that at least about 30% of said fibers have an average length which is from about 20% to about 40% of their length when in their original, unrefined state; preferably wherein from about 50% to about 90% of said fibers have an average length of from about 0.25 mm to about 1.5 mm.

The general definition of "refined" fibers herein is taken from the compilation of materials, in textbook form, available as SEMINAR—Refining of Chemical Pulps, Doshi & Associates, Inc., 2617 N. Summit Street, Appleton, Wis. 59414. According to this definition (at page 1), the "Purpose of Refining is to alter the fiber structure by the application of energy in the presence of water," or "mechanical treatment of chemical pulps to modify the fibers in such a way as to improve sheet properties."

M. R. Doshi (ibid. at 69) indicates that some of the changes in fiber properties associated with refining include internal fibrillation, external fibrillation and fiber shortening. Doshi states that the concomitant generation of "fines" or "crill" material is virtually inevitable.

It is to be understood that the refining process used herein is designed to minimize or, preferably, to avoid, fibrillation and to minimize, or preferably avoid, the formation of "fines".

All ratios, ranges and proportions herein are by weight, unless otherwise specified.

DESCRIPTION OF THE DRAWINGS

FIG. 6A is a cross-sectional view of an H-shaped capillary channel fiber in a partially collapsed state. While not optimal, such fibers can be used herein.

FIG. 6B is a cross-sectional view of an expanded capillary channel fiber. Such fibers can be used herein.

FIG. 6C is a cross-sectional view of a wholly collapsed capillary channel fiber. Such fibers are not used herein.

Figure 1:
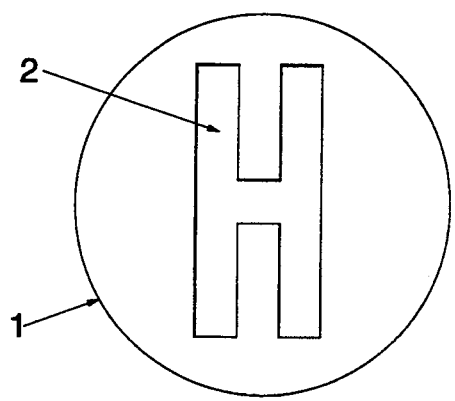
FIG. 1 is a direct view of an extrusion die (1) having an orifice (2) of a design suitable for making symmetrical "H" shaped capillary channel fibers having a planar base and capillary channels extending symmetrically from opposite sides of said base.

It is to be understood that FIGS. 1–6C are only for purposes of illustration and are not drawn to scale, inasmuch as the thickness of the walls and planar base of the capillary channel fibers can be, and preferably are, relatively much thinner than the width-between-walls. The thinner the walls and base, the more pliable the fiber, and the higher the fluid capacity.

FIG. 7 is a cross-sectional view of a catamenial pad with the view being along the longitudinal axis of the pad. The cross-section shows fluid-permeable topsheet (9), a layer or "secondary topsheet" (10) comprising the capillary channel fibers herein, a fluid retaining core (11), and a fluid impervious backsheet (12).

FIG. 8A is a cutaway perspective view of a catamenial pad having a fluid permeable topsheet (13), a fluid distributing capillary channel fiber layer, i.e., as a "secondary topsheet" (14) substantially covering a fluid retaining core (15) and a fluid impervious backsheet (16).

Figure 8B:
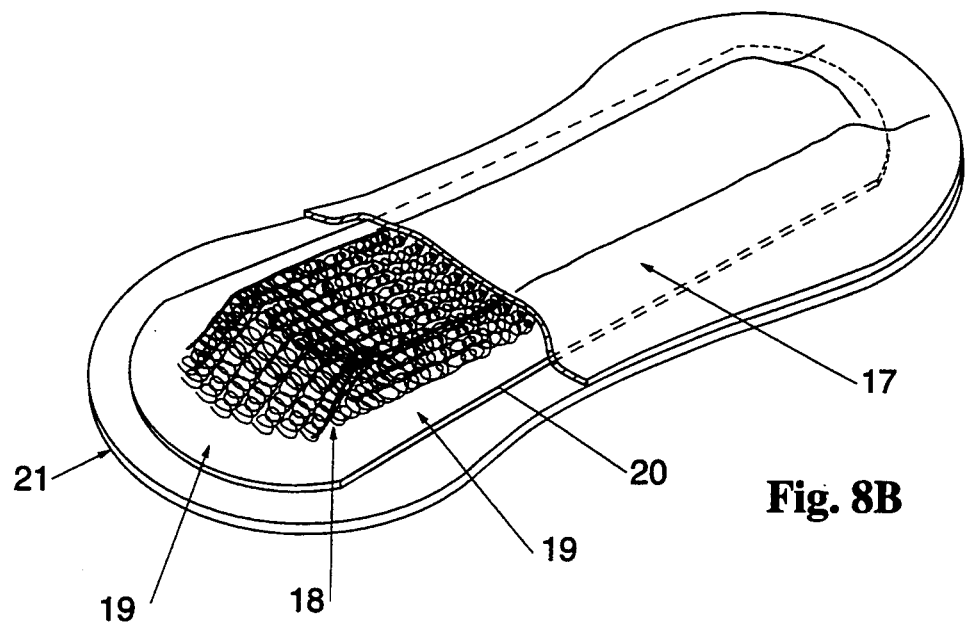

FIG. 8B is a cutaway perspective view of a catamenial pad having a fluid permeable topsheet (17) a capillary channel fiber layer (18) said layer not covering the peripheral edge (19) and terminating about one inch from the end of absorbent core (20). Backsheet (21) is also shown.

Figure 9:
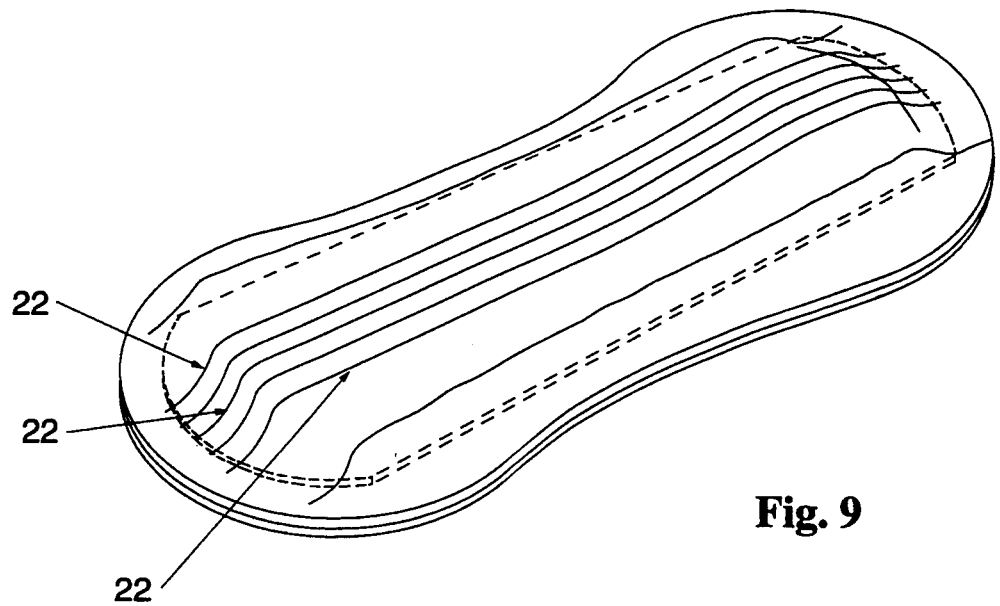

FIG. 9 is a perspective view of a catamenial pad wherein the contact between the various layers is achieved by multiple compression lines (22).

Figure 10:
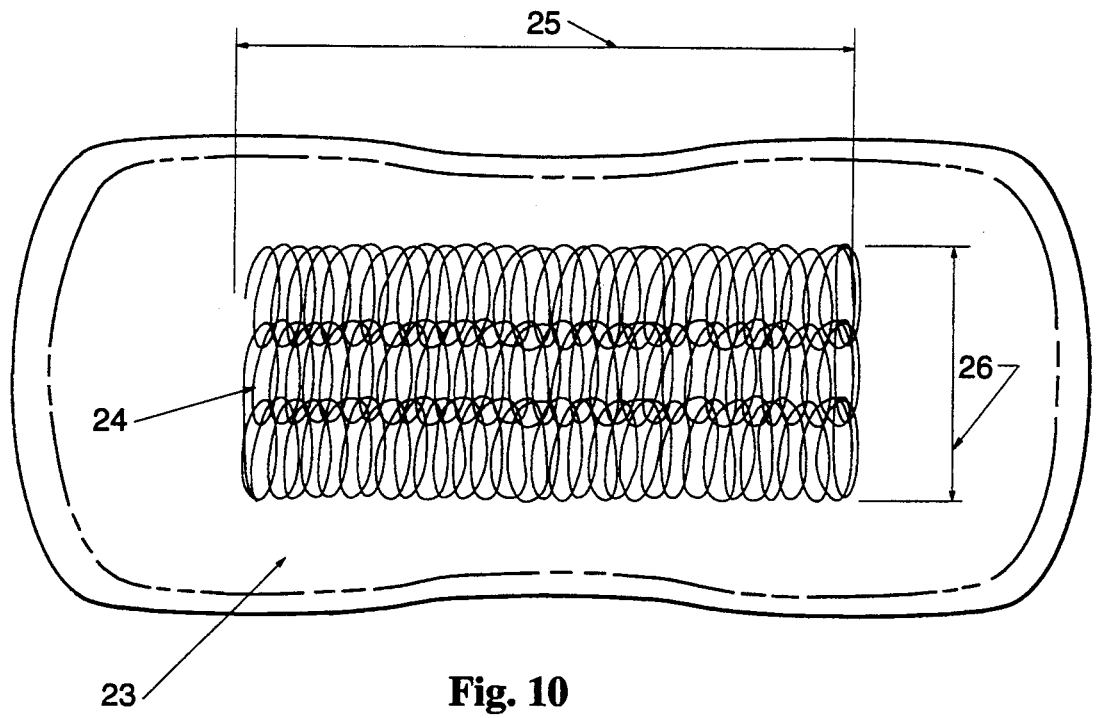

FIG. 10 illustrates the underside of a porous topsheet (23) and the preferred multispiral pattern of glue lines (24) used to affix the topsheet to the layer of capillary channel fibers. The machine direction dimension (25) of the pattern used on a typical catamenial is about 7 inches and the cross-direction dimension (26) is about 2 inches.

Figure 11:
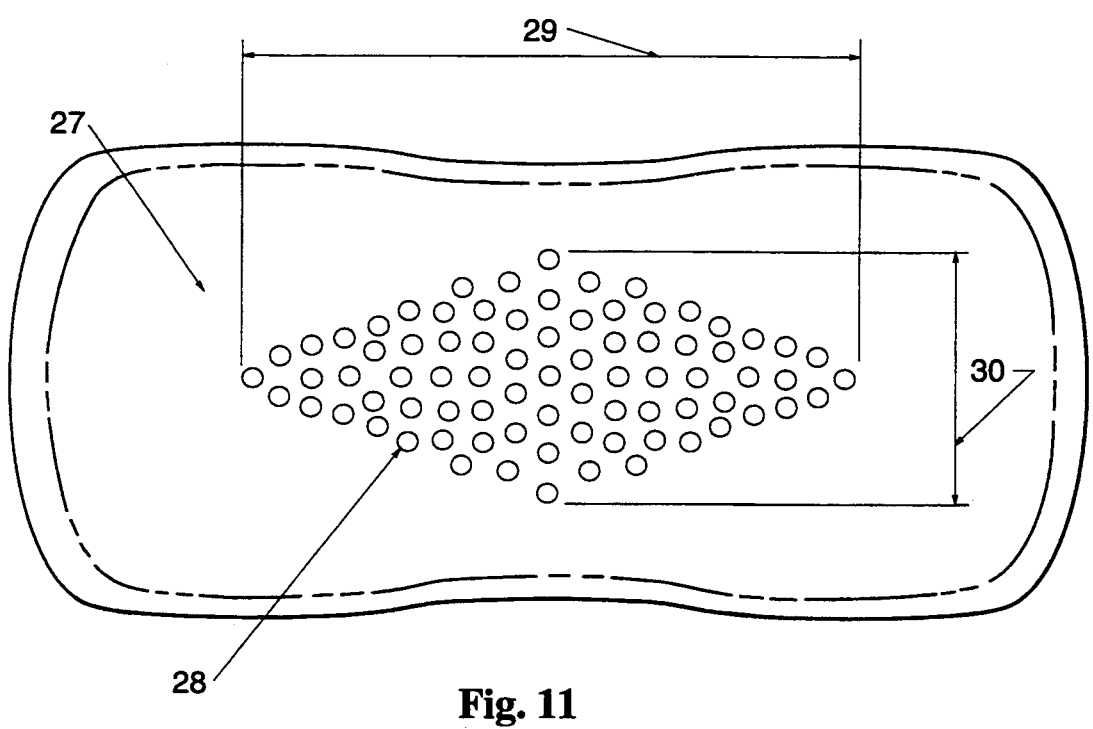

FIG. 11 shows the underside of a porous topsheet (27) and a pattern of adhesive spots (28) having machine direction dimension (29) and cross-direction dimension (30).

Figure 12:
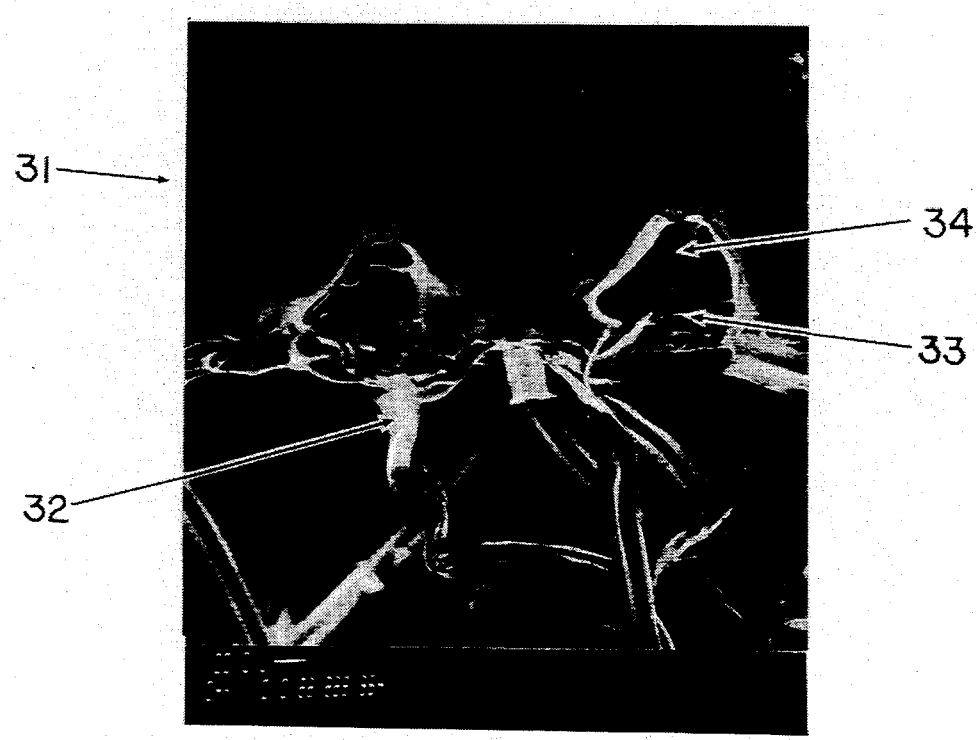

FIG. 12 is a photomicrograph of a section taken of formed film topsheet (31) and the layer of capillary channel fiber (32). The close contact between the capillary channel fibers and the topsheet is shown by the protrusion of capillary channel fibers (33) into pores (34) in the topsheet.

Figure 13:
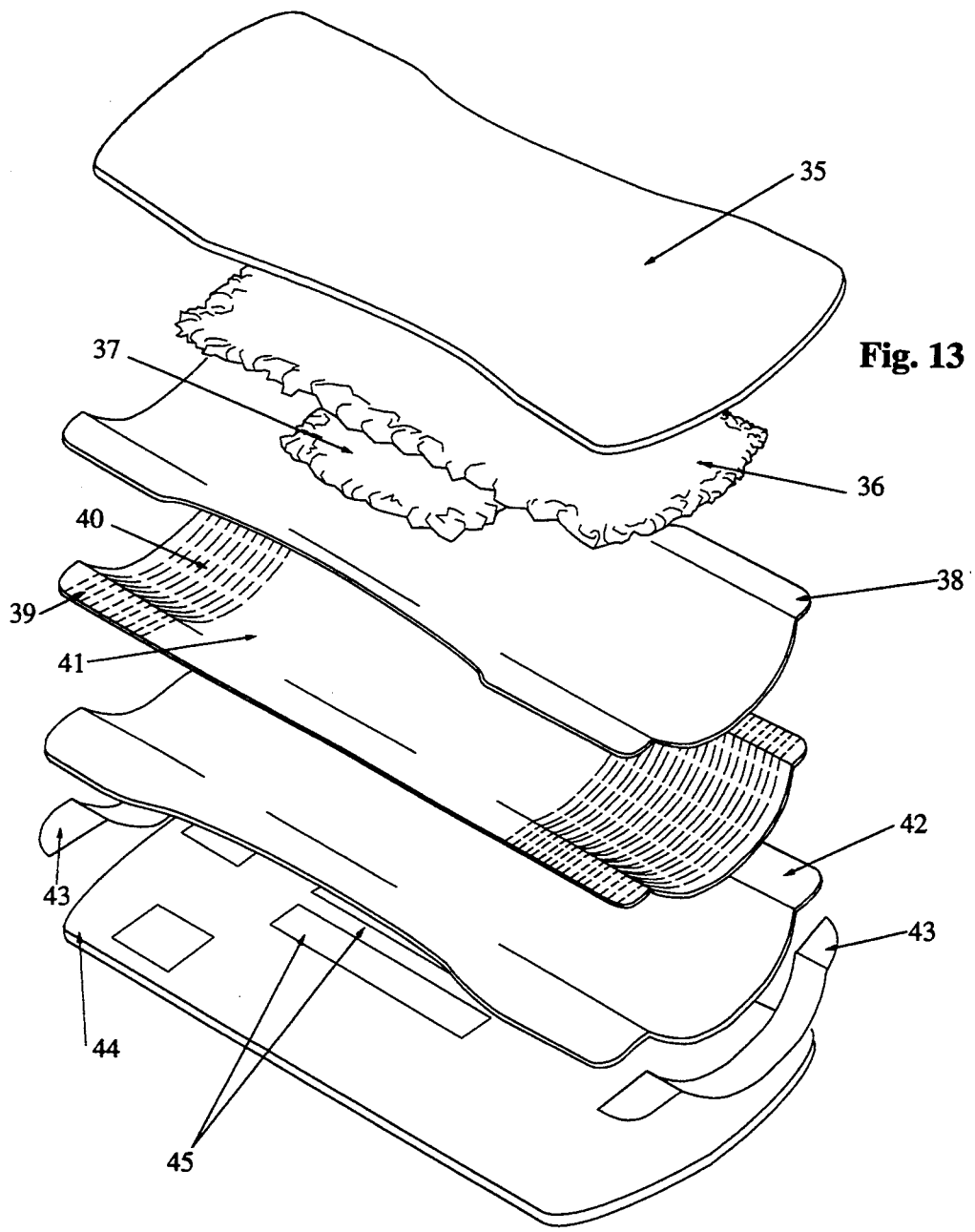

FIG. 13 is an exploded view of the sanitary napkin of Example I, with topsheet (35), a layer of CCF SW194 capillary channel fibers (36), a swatch of CCF SW173 capillary channel fibers (37) underlying layer (36), a creped paper towel (BOUNTY) layer (38), a wet-laid fibrous absorbent core (39) with slitted (40) and unslitted (41) areas and containing absorbent gelling material, backsheet (42) polyethylene end guards (43), optional release paper (44), and showing the relative placement of eight strips of panty fastening adhesive (45). In use, the panty fastening adhesive strips remain on the outer side of backsheet (42) when release paper (44) is removed from the article.

DETAILED DESCRIPTION OF THE INVENTION

The present invention refines curled, preferably chemically crosslinked and stiffened, twisted fibers and employs said refined fibers in sheet form as an absorbent core in catamenials. While the preparation of curled and twisted cellulosic fibers is known in the literature, and means for refining various fibers by the application of mechanical energy are well-known, it is not believed that refining procedures have heretofore been applied to curled fibers to achieve the benefits embodied in the present invention. The following describes the procedures and articles of this invention in more detail.

Fiber Manufacture—The preparation of suitable curled cellulosic fibers from which one can prepare the refined, curled and twisted cellulosic fibers used in the practice of this invention is described in great detail in U.S. Pat. Nos. 4,888,903; 4,822,543; 4,889,595; 4,889,597; 4,889,596; and 4,898,642. Use of such fibers in combination with absorbent gelling materials, and means for manufacturing such combinations, are described in U.S. Pat. No. 4,935,022. Such patents are cited hereinabove in the BACKGROUND ART section. Such preparations typically involve the use of aldehydes, such as glutaraldehyde, as crosslinking agents. In addition, polycarboxylic acids can be used as crosslinking agents; see the U.S. patent applications cited in the BACKGROUND ART section, hereinabove. It will be appreciated that other means for preparing other curled cellulosic fibers are also known, and such fibers may also be used herein, although the fluid absorbency properties may be suboptimal as compared with the above-mentioned fibers. Reference can also be made to the various citations in U.S. Pat. No. 4,898,642 and PCT U.S. 89 01581 for other fiber types.

The curled fibers prepared in the manner described in the cited references comprise individualized curled cellulosic fibers which are preferably chemically stiffened by means of a crosslinking agent. As described in U.S. Pat. No. 4,898,642, such curled fibers have an average dry fiber twist count of at least about 4.5 twist nodes per millimeter an average wet fiber twist count of at least about 3.0 twist nodes per millimeter and at least about 0.5 twist nodes per millimeter less than said dry fiber twist count; an average isopropyl alcohol retention value of less than about 30%; and an average water retention value of between about 28% and about 50%. Highly preferred fibers have an average dry fiber curl factor of at least about 0.30, more preferably at least about 0.50. It is to be understood that the refining process herein does not substantially affect the foregoing parameters, inasmuch as the process is carried out in such a manner that there is little or no defibrillation of the original curled and twisted fibers. Rather, the original fibers are, in general, reduced in length. On average, the original curled fibers employed herein have lengths ranging approximately from about 1.6 mm to about 7 mm. After refining in the manner disclosed herein, at least about 30% of the resulting fibers, preferably at least about 50%, more preferably from about 50% to about 90%, most preferably at least about 90% of the refined fibers have an average length which is from about 20% to about 40% of the length of the original, unrefined curled fibers. Stated otherwise, on average the unrefined fibers prepared by the above-referenced processes will have lengths in the range from about 1.6 mm to about 1 mm, whereas, after refining, the lengths of the fibers will typically be mainly in the average range from about 0.25 mm to about 1.5 mm.

Figure 2:
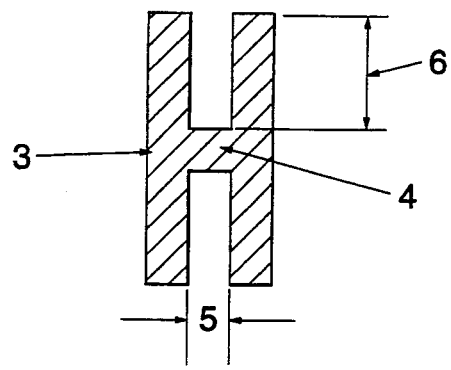
FIG. 2 is a cross-sectional view of a symmetrical "H" shaped capillary channel fiber (3) with planar base (4), width-between-walls (5) and depth-of-walls (6) made by the extruding a polymer through the die of FIG. 1.
Figure 3:
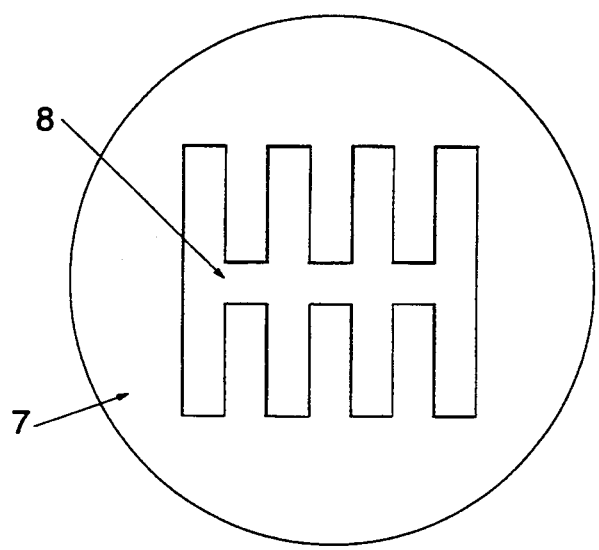
FIG. 3 is a direct view of an alternate extrusion die (7) having an orifice (8) design suitable for making "multiple H" shaped capillary fibers having a planar base and multiple capillary channels extending symmetrically from opposite sides of said base and all optionally having approximately the same channels widths and heights.
Figure 4:
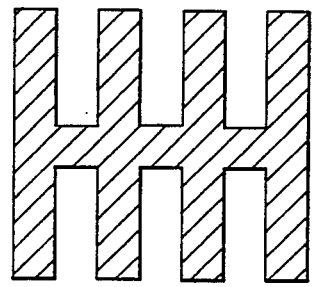
FIG. 4 is a cross-sectional view of a capillary channel fiber made by the extruding a polymer through the die of FIG. 3.
Figure 5:
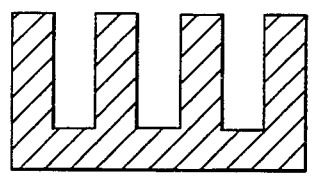
FIG. 5 is a cross-sectional view of a multiple " "-shaped fiber.

Fiber Refining—Once prepared by any of the aforementioned, art-disclosed processes, the curled cellulosic fibers are refined to provide the fibers used in the practice of this invention; see FIG. 2.

In a typical process, an aqueous stock comprising about 3% by weight of said fibers and 97% by weight water is passed through a Sprout-Waldron (now available as Sprout-Bauer) single disk refiner (available from Koppers Company, Inc., Muncy, Pa., Model 105A-LAB) using a deknotting disk of the 17804-A type. Importantly, it is the objective of the refining process herein to cut the twisted fibers without substantially defibrillating them.

The 3% aqueous stock solution is diluted to 0.5% consistency and flows through the Sprout-Waldron refiner using a gap setting of from about 5 mils to about 30 mils, preferably about 2.5 mils. (Note: The Sprout-Waldron is modified by removing the equalizing spring so that the gap setting remains constant throughout the flow of the fibrous stock solution). Typical flow rate is 9-10 gallons per minute and the refining amperage is about 45 on a 25 hp. motor. (Use of the amperage term is a measure of the mechanical energy imparted to the fibers during the refining). A single pass of the fibers through the gap is employed.

In an alternate mode, the curled cellulosic fibers can be used in combination with crill, which is a highly refined southern softwood kraft fiber having a freeness of pulp between about 50 to about 100 ml. as determined in accordance with the Technical Association of the Pulp and Paper Industry (TAPPI). Typically, the crill comprises up to about 5%-10% by weight of the curled cellulosic fibers. Addition of crill can impart desirable strengthening properties to the final sheets, and also can serve as a diluent in the sheets, for reasons of economy.

Following the refining step, the 0.5% aqueous slurry of the refined, twisted fibers is further diluted to a slurry weight of from about 0.1%-0.2% for use in the Sheet Formation operation, hereinafter.

Sheet Formation—In general terms, the formation of the above-prepared refined, curled cellulosic fibers into sheets suitable for use as the absorbent core in catamenials, and the like, employs a Fourdrinier papermaking process with a standard fixed roof forming technique, and involving vertical transfer of the sheet across a through-air dryer. See, for example, U.S. Pat. No. 4,889,597. In the process, a breast roll is employed in the manner known in the art for preparing facial tissue, filter paper, and the like. However, unlike the manufacture of filter paper, the sheet herein is dried without substantial pressure; rather, the through-air dryer system is employed.

In more detail, the above-described aqueous slurry comprising from about 0.1% to about 0.2% by weight of the refined, curled cellulosic fibers is introduced from the head box of the papermaking machine onto a standard forming wire. An objective is to avoid fiber flocculation, which would result in a nonuniform lay-down of fibers in the resulting sheet. The distance between the top of the head box and the forming wire (the "slice setting") is preferably set at about 90 mils to avoid flocculation. The dilution water can also be adjusted to avoid flocculation by settling. As noted, avoiding flocculation results in sheets having a substantially uniform distribution of fibers.

Dewatering of the sheet is relatively rapid down to the 23% level. A vacuum box is employed to remove any excess water from the forming wire, after which the sheet is transferred to a drying fabric. Drying is accomplished using a standard through-air dryer with an air temperature of about 300° F. This results in a sheet having about 3%-4% by weight moisture, which can requilibrate (depending on ambient humidity) to 8%-10% moisture. It should be noted that the sheet is preferably not compacted during drying, since this interferes with the absorbency capacity. While the sheet formed in the foregoing manner is quite absorbent and suitable for use in many absorbent structures, it will be appreciated that such sheets may be somewhat stiffer than desired by the formulator of sanitary napkins and pantiliners. Using standard techniques, the sheets can be calendered and/or passed through rollers in an "S" configuration to flex the sheet to the point that it becomes soft and pliable to the touch. This can be repeated, according to the desires of the formulator.

It is to be understood that the sheets prepared in the foregoing manner are highly absorbent and quite suitable for use in catamenial products. However, the sheets may lack strength for some purposes, especially when moistened and subjected to stresses, e.g., during wear by the user. In order to overcome this problem, it has been determined that a thin scrim of commercially available nonwoven, extremely porous, very low basis weight polypropylene, such as AMOCO D2 scrim, for example, can be laid down on the forming wire of the Fourdrinier, after which the refined, curled fibers are formed into a sheet on top of the scrim. During formation of the sheet on such a scrim, small amounts of the fibers pass through the scrim and attach the sheet to the scrim by a phenomenon referred to in the art as "stapling". Preparing the sheet/scrim by this process is preferred over the alternative process which would involve forming the sheet, placing the scrim on top of the sheet, and subjecting the resulting scrim/sheet to vacuum. In this latter type of process it has been noted that good "stapling" does not occur, and the scrim tends to decouple from the sheet.

The following Examples further illustrate the practice of this invention, but are not intended to be limiting thereof.

EXAMPLE I

Individualized, stiffened, curled cellulosic fibers are prepared according to the procedure of EXAMPLE I of U.S. Pat. No. 4,898,642 and are refined in the foregoing manner. The resulting slurry of refined fibers is formed into a tissue sheet having a Basis Weight (weight per 3,000 ft.$^2$) of 35 pounds. The sheet can be used, for example, in a tissue laminate having a central layer of polyacrylate absorbent gelling material. Such laminates typically comprising about 0.68 grams of the absorbent gelling material are useful as the absorbent core in ultra-thin sanitary napkins.

EXAMPLE II

Individualized, crosslinked fibers are made by a dry crosslinking process utilizing citric acid as the crosslinking agent. The procedure used to produce the citric acid crosslinked fibers is as follows:

1. For each sample, 1735 g of once dried, southern softwood kraft (SSK) pulp is provided. The fibers have a moisture content of about 7% (equivalent to 93% consistency).

2. A slurry is formed by adding the fibers to an aqueous medium containing about 2,942 g of citric acid and 410 ml of 50% sodium hydroxide solution in 59,323 g H$_2$O. The fibers are soaked in the slurry for about 60 minutes. This step is also referred to as "steeping". The steep pH is about 3.0.

3. The fibers are then dewatered by centrifuging to a consistency ranging from about 40% to about 50%. The centrifuged slurry consistency of this step combined with the carboxylic acid concentration in the slurry filtrate in step 2 set the amount of crosslinking agent present on the fibers after centrifuging. In this example, about 5 weight % of citric acid, on a dry fiber cellulose anhydroglucose basis is present in the fibers after the initial centrifuging. In practice, the concentration of the crosslinking agent in the slurry filtrate is calculated by assuming a targeted dewatering consistency and a desired level of chemicals on the fibers.

4. Next, the dewatered fibers are defibrated using a Sprout-Waldron 12″ disk refiner (model number 105-A) whose plates are set at a gap which yields fibers substantially individualized but with a minimum amount of fiber damage. As the individualized fibers exit the refiner, they are flash dried with hot air in two vertical tubes in order to provide fiber twist and curl. The fibers contain approximately 10% moisture upon exiting these tubes and are ready to be cured. If the moisture content of the fibers is greater than about 10% upon exiting the flash drying tubes, then the fibers are dried with ambient temperature air until the moisture content is about 10%.

5. The nearly dry fibers are then placed on trays and cured in an air-through drying oven for a length of time and at a temperature which in practice depends on the amount of citric acid added, dryness of the fibers, etc. In this example, the samples are cured at a temperature of about 188° C. for a period of about 8 minutes. Crosslinking is completed during the period in the oven.

6. The crosslinked, individualized fibers are placed on a mesh screen and rinsed with about 20° C. water, soaked at 1% consistency for one (1) hour in about 60° C. water, screened, rinsed with about 20° C. water for a second time, centrifuged to about 60% fiber consistency, and dried to an equilibrium moisture content of about 8% with ambient temperature air. The resulting individualized citric acid-crosslinked cellulosic fibers are refined in the above-described manner, and are formed into a sheet on an Amoco D2 scrim, at a sheet/scrim Basis Weight of 150 pounds. After softening by passage over S-rolls, the sheet/scrim is suitable for use as the absorbent core in a sanitary napkin.

EXAMPLE III

Individualized crosslinked fibers are made by a dry crosslinking process utilizing 1,2,3,4 butane tetracarboxylic acid (BTCA) as the crosslinking agent. The individualized crosslinked fibers are produced in accordance with the hereinbefore described process of Example II with the following modifications: The slurry in step 2 of Example II contains 150 g of dry pulp, 1186 g of $H_2O$, 64 g of BTCA and 4 g of sodium hydroxide. In step 5, the fibers are cured at a temperature of about 165° C. for a period of about 60 minutes.

The resulting fibers are refined and formed into a sheet/scrim in the manner of Example II for use herein.

EXAMPLE IV

Individualized crosslinked fibers are made by a dry crosslinking process utilizing 1,2,3 propane tricarboxylic acid as the crosslinking agent. The individualized crosslinked fibers are produced in accordance with the hereinbefore described process of Example II with the following modifications: The slurry in step 2 of Example II contains 150 g of pulp, 1187 g of water, 64 g of 1,2,3 propane tricarboxylic acid, and 3 g of sodium hydroxide. In step 5, the fibers are cured at a temperature of about 165° C. for a period of about 60 minutes.

The resulting fibers are refined and formed into a sheet/scrim in the manner of Example II for use herein.

EXAMPLE V

Individualized crosslinked fibers are made by a dry crosslinking process utilizing oxydisuccinic acid as the crosslinking agent. The individualized crosslinked fibers are produced in accordance with the hereinbefore described process of Example II with the following modifications: The slurry in step 2 of Example II contains 140 g of pulp, 985 g of water, 40 g of sodium salt of oxydisuccinic acid, and 10 ml of 98% sulfuric acid.

The resulting fibers are refined and formed into a sheet in the manner of Example II for use herein.

EXAMPLE VI

Individualized crosslinked fibers are made by a dry crosslinking process utilizing citric acid as the crosslinking agent and sodium sulfate as the catalyst. The individualized crosslinked fibers are produced in accordance with the hereinbefore described process of Example II with the following modifications: The slurry as described in step 2 of Example II contains 200 g of pulp, 7050 g of $H_2O$, 368 g of sodium sulfate and 368 g of citric acid. The steep pH is about 2.0. In step 5, the fibers are cured at a temperature of about 165° C. for a period of about 60 minutes.

The resulting fibers are refined as above and formed into a sheet/scrim having a Basis Weight of about 83 pounds. After softening by passage over S-rolls, the sheet is suitable for use as the absorbent core in a pantiliner.

EXAMPLE VII

Individualized crosslinked fibers are made by a dry crosslinking process utilizing citric acid as the crosslinking agent and sodium hypophosphite as the catalyst. The individualized crosslinked fibers are produced in accordance with the hereinbefore described process of Example II with the following modifications: The slurry as described in step 2 of Example II contains 326 g of pulp, 138 g of sodium hypophosphite, 552 g of citric acid and 78 g of NaOH in 10,906 g of $H_2O$. In step 5, the fibers are cured at a temperature of about 188° C. for a period of about 6 minutes.

The resulting fibers are refined and formed into a sheet/scrim having a density of about 0.125 (at 0.1 psi pressure) and a capacity for sheep's blood of about 8.0 grams blood/gram of sheet. Such sheets are useful at various Basis Weights in sanitary napkins and pantiliners.

The preparation of sanitary napkins, pantiliners, and the like products, using the aforesaid sheets or, preferably, sheet-scrim combinations comprising the refined fibers involves interposing one or more of said sheets between a fluid-permeable topsheet and a fluid-impermeable backsheet. The manufacture of such products is well-known in the literature and commercial practice. The following is included herein for the convenience of the formulator in selecting suitable topsheet and backsheet materials.

Fluid Receiving Topsheets—The finished articles herein are provided with a fluid-receiving topsheet. Such topsheets are made of materials which are preferably hydrophobic, but fluid-permeable. Topsheet materials of the type employed in the practice of this invention can be prepared by methods well-described in the patent literature. For example, according to the process of U.S. Pat. No. 4,324,246, Mullane and Smith, Apr. 13, 1982, a sample of thermoplastic material such as 0.0038 cm thick polyethylene film is heated above its softening point. (The softening point is the temperature at which the thermoplastic material can be formed or molded and is less than the melting point of the material). The heated thermoplastic material in sheet form is then brought into contact with a heated forming screen. The forming screen is preferably an apertured wire mesh screen having the desired aperture size, pattern and configuration. A vacuum is used to draw the heated film against the forming screen, thereby forming the film into the desired pattern and having the desired hole sizes. While the vacuum is still being applied to the film, a jet of hot air is passed over the film. The hot air jet perforates the film in a pattern corresponding to the pattern and size of apertures in the forming screen.

Fluid-permeable topsheets prepared in the manner of the Mullane et al patent are conveniently referred to as "formed films". The caliper of such films is important since, if the caliper is too great, liquid may accumulate in the apertures and not readily pass there through. For the manufacture of absorbent articles such as diapers, catamenials, incontinence articles, and the like, the topsheets typically have a caliper of less than about 0.075 cm, or preferably less than about 0.064 cm.

Another formed-film sheet material useful as the topsheet herein is the resilient, 3-dimensional web exhibiting a fiber-like appearance and tactile impression, comprising a fluid-impervious plastic material, with said web having a multiplicity of apertures, the apertures being defined by a multiplicity of intersecting fiber-like elements, all as disclosed in U.S. Pat. No. 4,342,314, Radel and Thompson, Aug. 3, 1982. The Radel and Thompson sheet materials can be prepared using hydrophobic plastics such as polyethylene, polypropylene, PVC, and the like, and are well-known for use in absorbent products such as catamenials, and the like.

Yet another type of formed-film sheet material useful herein is described in U.S. Pat. No. 3,929,135, Thompson, Dec. 30, 1975, and consists of hydrophobic polymer films having holes which are in the form of tapered capillaries. These "tapered capillary" topsheets are also known for use in absorbent articles, including adult incontinence articles. They may be prepared from various hydrophobic polymers, as mentioned hereinabove; typically, low density polyethylene having thickness of from 0.0025 to 0.0051 cm is employed.

Reference to U.S. Pat. No. 3,929,135 can be made in order to further visualize tapered capillary topsheets. In use, the apices of the capillaries in such tapered capillary topsheets are in contact with the underlying absorbent core material. Generally, tapered capillaries are in the form of a frustrum of a conical surface, but it is to be understood that any generally tapered structure, such as a frustrum of a pyramid or the like with a triangular, square, or polygonal base, is within the term "tapered capillary"; circular tapered capillaries, however, are used in this description for convenience. It is also to be understood that the tapered capillaries can be asymmetric (i.e., the angle of taper on one side can be different from that on another side) and that the angle of taper can change continuously (i.e., be curved) over the distance from base to apex. In the latter case, the angle of taper is defined as the angle of the tangent to the side of the capillary at its point of minimum apex opening dimension. The angle of taper suitable for use in topsheets according to the practice of this invention is from about 10° to about 60°.

Base opening dimension of the capillaries is defined as the maximum open measurement in the plane of topsheet at said tapered capillary. Apex opening dimension is defined as the maximum open measurement in the apex of said tapered capillary, which apex is remote from the plane of the topsheet. When the tapered capillary is in the form of a frustrum of a conical surface, the base and apex opening dimensions are, respectively, the base diameter and the apex diameter. Base diameter and apex diameter are hereinafter used interchangeably with, respectively, base opening dimension and apex opening dimension.

The tapered capillary apex diameter is a diameter which will allow liquid to readily pass from the surface of the topsheet to the underlying absorbent core. The apex diameter is from about 0.004 to about 0.100 inch (0.010 to 0.254 centimeter), preferably from about 0.005 to about 0.020 inch (0.013 to 0.051 centimeter).

The tapered capillary base diameter is selected to satisfy two criteria. The first of these is the subjective feel of the surface of the topsheet which contacts the skin of the user. It has been discovered that polyethylene can be made to exhibit pleasing, cloth-like, non-waxy attributes when the base diameter is within the range from about 0.006 to about 0.250 inch (0.015 to 0.635 centimeter). Preferably, the base diameter should be within the range of from about 0.030 to about 0.060 inch (0.076 to 0.152 centimeter). The second criterion is that the capillary base diameter be small enough to allow an expected liquid droplet to bridge across at least one capillary. This criterion is satisfied by the above dimensions for disposable diapers and sanitary items.

The height of the tapered capillary is defined as the distance between the outermost surface of the topsheet (i.e., that surface which normally contacts the skin of the user) and the apex of the tapered capillary. This height, of course, depends upon apex diameter, base diameter, and angle of taper which have been selected as hereinbefore described. The height of the tapered capillary should provide a structure with a minimum tendency to collapse in use. The characteristics of the material of construction of the topsheet in large measure determine suitable ranges for the height. When the topsheet is low density polyethylene of from 0.001 to 0.002 inch (0.003 to 0.005 cm) thickness and apex diameter and base diameter are in the preferred range, and angle of taper $\alpha$ is in its critical range, the height of the tapered capillary can be from about 0.003 to about 0.159 inch (0.008 to 0.404 centimeter).

A state of relative dryness on the surface of the topsheet implies that most of the liquid which contacts the topsheet is transferred through it to the absorbent element. This in turn implies that each isolated droplet of fluid in contact with the topsheet must be in contact with the base diameter of a tapered capillary. This state of affairs can best be achieved if the land area (the area of the topsheet that exists between the bases of the tapered capillaries) is maintained at a minimum. The minimum limiting value is the case where conical tapered capillaries or pyramid's tapered capillaries are provided in close packed array (where the periphery of the base of each capillary is in contact on all sides with the periphery of the base of adjacent capillaries). The preferred arrangement of minimum land area tends to insure that an individual droplet will contact at least one tapered capillary. A preferred arrangement in disposable diapers is where the tapered capillaries as hereinbefore described are in ordered arrangement with from about 30 to about 1500 tapered capillaries per square inch of topsheet (5 to 231 per square centimeter).

Tapered capillary sheets can be manufactured in any of several ways well known in the art. One particularly suitable method is to provide a heated mold with male elements of the shape and arrangement of the desired tapered capillaries (hereinafter a pin mold). Each male element is secured in such a fashion that its apex extends away from the base of the pin mold. A portion of sheet material is brought into contact with the heated pin mold between the mold and a resilient backing plate. Pressure is applied to the combination of mold, sheet and resilient back plate and tapered capillaries are formed in the sheet to make the tapered capillary topsheet. An alternate way of constructing the topsheet is to subject a portion of liquid-impervious material to vacuum forming over an appropriate mold. After forming tapered capillary sheets in one of the aforementioned ways, it may be necessary to physically remove material from the apices of the capillaries so as to insure that the apex diameters are the desired value. Such removal of material can be accomplished by, for example, subjecting the apices to controlled abrasion or by heating the formed topsheet so as to melt open the apices. See, also, U.S. Pat. No. 4,629,643, Curro and Linman, Dec. 16, 1986, for a microapertured polymeric film with improved tactile impression, which can also be used in the practice of this invention.

A highly-preferred fluid-permeable formed-film topsheet material which can be employed in the practice of this invention is disclosed in U.S. Pat. No. 4,463,045, Ahr et al, Jul. 31, 1984, and reference can be made to that patent to further assist visualization of the Ahr et al structures.

In general terms, the topsheets provided by U.S. Pat. No. 4,463,045 are designed not only to provide a desirable cloth-like tactile impression, but also to substantially eliminate surface gloss. Thus, topsheets made of plastic do not have an undesirably shiny, "plasticky" appearance.

Such highly-preferred topsheet materials can be succinctly described as being a macroscopically expanded three-dimensional plastic "web" having at least one visible surface which appears substantially non-glossy when exposed to light, substantially all of said visible surface exhibiting a regularly spaced, microscopic pattern of discrete surface aberrations, each of said surface aberrations having its amplitude oriented perpendicular to the surface in which said surface aberration originates, each of said surface aberrations having a maximum dimension of less than about 6 mils, as measured in a plane oriented substantially perpendicular to its amplitude, whereby said surface aberrations are not discernible to the normal naked eye when the perpendicular distance between the viewer's eye and the plane of said web is at least about 12 inches, each of said surface aberrations also being free of planar areas which are large enough to inscribe a 4 mil diameter circle and so spaced relative to all adjacent surface aberrations that the maximum diameter of any circle which can be inscribed on any planar surface intermediate said surface aberration and said adjacent surface aberrations on any portion of said visible surface is less than about 4 mils, whereby any light incident upon any portion of said visible surface is diffusely reflected into a multiplicity of directions by said surface aberrations so that said visible surface appears substantially non-glossy.

The '045 topsheet materials can have at least a portion of said surface aberrations comprising protuberances projecting generally outwardly from the surface, and can have at least a portion of said surface aberrations comprising depressions projecting generally inwardly from the surface of said web.

The manufacture of these preferred topsheets can be achieved by use of a forming screen or structure, as generally noted hereinabove, which provides said surface aberrations by virtue of "knuckles" on the support member. (The preparation of such sheets is described in great detail in U.S. Pat. No. 4,463,045, and their method of preparation forms no part of this invention). In general, the resulting surface aberrations correspond to the knuckles of a woven mesh support structure which directly contacts the visible surface of said plastic sheet during production thereof.

In a preferred manufacturing method, the woven mesh support structure which directly contacts the visible surface of said topsheet is comprised of filaments having a diameter between about one and about two mils and a mesh count between about 160 filaments per lineal inch (2.54 cms) by 160 filaments per lineal inch (2.54 cms) and about 400 filaments per lineal inch (2.54 cms) by 400 filaments per lineal inch (2.54 cms).

Preferred topsheets herein are those wherein said surface aberrations have an average amplitude of at least about 0.2 mils, more preferably at least about 0.3 mils. Most preferably, topsheets having an amplitude of each of said surface aberrations, as measured perpendicular to the surface in which said surface aberration originates, within the range of about ±20%, desirably ±10%, of the average value of the amplitude for all adjacent surface aberrations are used.

"One-way" formed-film topsheets whose backfaces are treated with hydrophilic latex are described in U.S. Pat. No. 4,735,843, Noda, Apr. 5, 1988, and these can also be employed herein.

In addition to the sophisticated apertured materials mentioned hereinabove, the practice of the present invention may also be undertaken with hydrophobic sheet materials having simple holes punched there through.

It will be understood from the foregoing that the aforesaid, preferred, "sheet" or "film" materials used as the topsheet in the practice of this invention are substantially different from fibrous nonwoven materials, which are characterized by a large number of fibers which overlap each other throughout the thickness of the material. Moreover, the formed-film topsheet materials used herein are made from materials (preferably, hydrophobic thermoplastic polymeric materials) which provide a clean-appearing, stain-resistant or "non-staining" surface, in use. Such topsheets (as well as fibrous topsheets) can be rendered hydrophilic by spraying on surfactants, e.g., PEGOSPERSE, in well-known fashion.

It will also be appreciated that fibrous, nonwoven topsheets made from materials such as polyethylene, polypropylene and blends are commonly used in commercial sanitary napkins and pantiliners, and such fibrous topsheets can also be used herein.

Such "fibrous", i.e., non-formed-film, topsheet materials which can be used herein include, for example, various nonabsorbent fibrous or filamentous network sheets which are aqueous-fluid-permeable by virtue of a multiplicity of holes or channels passing therethrough. Such sheet materials can be prepared by methods well-described in the patent literature. For example, according to the process of U.S. Pat. No. 4,636,419, Madsen et al, Jan. 13, 1987, sheets comprising a network of ribboned filaments of two dissimilar chemical types, and with two dissimilar melting or softening points, are contacted and cooled to allow the formation of a network sheet characterized by said different transverse and longitudinal polymer materials. Such sheets can be used in the practice of this invention.

Another sheet material useful herein is the formaminous net comprising a reticular network of polymeric filaments, said net comprising two arrays of filaments oriented at a displacement angle of 20-90 degrees. Reference can be made to European Patent Application 0215417, filed Jun. 09, 1986, Sneyd et al, to further assist visualization of this sheet. The aforesaid sheet materials can be prepared using hydrophobic plastics such as polyethylene, polypropylene, PVC, and the like, and are well-known for use in absorbent products such as catamenials, and the like. Such sheet materials typically have a basis weight of 0.5-5.0 ounces/yd$^2$ (0.0016 g/cm$^2$-0.016 g/cm$^2$), a caliper of 5-25 mils, an open area of 30-80% and a mesh of 20-40. Conventional nonwoven topsheets can also be employed.

Backsheet—The backsheet is conventional, and can comprise a fluid-impermeable polymer sheet, for example polyethylene or polypropylene, that is thin enough to be flexible. A polyethylene sheet 0.001 mm-0.5 mm thick is typical. Flushable or biodegradable backing sheets can also be used, e.g., with pantiliner devices herein.

Optional Retaining Means—The absorbent structures herein can optionally, but preferably, be provided with means to hold them in place on or near the user's body to allow the structures to perform their intended function. For example, sanitary napkins can be provided with glue stripes facing outward on their backsheet in well-known fashion. Various pins, clips and fasteners of well-known types can optionally be employed.

The following Examples illustrate the use of absorbent sheets prepared in the manner of this invention in disposable sanitary products.

EXAMPLE VIII

A lightweight pantiliner suitable for use between menstrual periods comprises a substantially rectangular pad having a surface area of about 117 cm$^2$ and containing the sheet/scrim of Example VI herein as the absorbent core. The sheet is interposed between the formed-film topsheet of U.S. Pat. No. 4,463,045 and a flexible polyethylene backsheet. The pantiliner functions to absorb vaginal discharges without the need for absorbent gelling materials.

EXAMPLE IX

A catamenial product in the form of a sanitary napkin having two flaps extending outward from its absorbent core is prepared using the absorbent sheet of Example VII, herein, per the design of U.S. Pat. No. 4,687,478, Van Tilburg, Aug. 18, 1987. The absorbent core comprises a sheet/scrim having a Basis Weight of about 150 pounds. The nonglossy sheet of U.S. Pat. No. 4,463,045 is used as the topsheet.

EXAMPLE X

The preparation of a thin sanitary napkin is as follows. An absorbent core is prepared in the manner of Example VII at a Basis Weight of about 150 pounds. The core is cut to a size of about 8.0 in. $\times$ 2.75 in., and is placed on top of a slightly larger piece of polyethylene backsheet. An additional piece of tissue is positioned on top of the core. The formed-film topsheet of the type disclosed in U.S. Pat. No. 4,463,045 is coated evenly on its underside with ca. 0.03 g of a latex adhesive, and excess adhesive is wiped off. The topsheet is rolled with a glass rod to ensure good contact and proper application of adhesive. The topsheet is then placed on top of the above-prepared core assembly. To ensure good core bonding, the topsheet is weighted with a piece of plexiglas. The assembly is sealed together to provide the overall product: topsheet/tissue/absorbent core/backsheet. Optionally, adhesive can be applied on the outside of the backsheet of the pad for affixing the article to undergarments. The topsheet of the product is sprayed with about 0.03 g of PEGOSPERSE 200 ML, a polyethylene glycol 200 monolaurate available from Lonza, Inc., Williamsport, Pa., USA) surfactant to hydrophilize the fluid-receiving surface of the topsheet.

The following Examples illustrate the use of the absorbent core of this invention in conjunction with capillary channel fibers which serve to direct fluid and prevent leakage of the fluid from the sides of the article onto the user's undergarments. The principles of fluid-directing capillary channel fibers are discussed in EPO Application 391,814, Phillips et al, published Oct. 10, 1990. Suitable capillary channel fibers are available from Eastman Chemicals as "SW194" and "SW173" CCF fibers.

It is to be understood that the manufacture of capillary channel fibers of the type employed herein forms no part of this invention. Attention is drawn to EPO Application 391,814 (cited above) or to its co-pending continuation-in-part U.S. application entitled "FIBERS CAPABLE OF SPONTANEOUSLY TRANSPORTING FLUIDS", Ser. No. 07/736,267, filed Jul. 23, 1991, Inventors Phillips, Jones, et al, Eastman Chemical Company, or to the co-pending U.S. patent application entitled "OPEN CAPILLARY CHANNEL STRUCTURES, IMPROVED PROCESS FOR MAKING CAPILLARY CHANNEL STRUCTURES, AND EXTRUSION DIE FOR USE THEREIN", Ser. No. 07/482,446, filed Feb. 20, 1990, Inventors Thompson and Krautter, all incorporated herein by reference, for further details regarding means for manufacturing capillary channel fibers. See, also, the concurrently-filed U.S. patent applications of Thompson et al, entitled "FLUID HANDLING STRUCTURE FOR USE IN ABSORBENT ARTICLES", Ser. No. 07/734,392, filed Jul. 23, 1991, and Thompson et al, entitled "ABSORBENT ARTICLES, ESPECIALLY CATAMENIALS, HAVING IMPROVED FLUID DIRECTIONALITY, COMFORT AND FIT", Ser. No. 07/734,404, filed Jul. 23, 1991, incorporated herein by reference for the design of absorbent articles.

As a point of reference, and in accord with common practice, the long (or "x") axis is of typical pad-type catamenials is referred to as the "machine direction", inasmuch as, during manufacture the articles pass through the machine in the direction of this axis. The short (or "y") axis is referred to as the "cross direction", since it is the direction across the width of the article.

The "z" direction is the direction proceeding down through the topsheet, thence into the layer of capillary channel fibers, and thence into whatever fluid storage core that may be provided. The objective is to provide a gradient of capillary suction between the topsheet and underlying layer or layers of the articles herein, such that fluid is drawn in the "z" direction and away from the surface of the article into its ultimate storage layer. Empirically, capillary suction is related to adhesion tension and inversely related to the size of the openings—i.e., in the typical case, the openings in the topsheet will be larger than the intra-fiber capillary channels, which, in turn, will be larger than the inter-fiber capillary channels in a fibrous storage core. The surface hydrophilicity of the components of each layer can theoretically affect the capillary suction gradient.

Simply stated, the capillary channel fibers optionally used herein promote passage of fluids in the "z" direction of absorbent articles. Moreover, by employing a layer of capillary channel fibers whose fibers are positioned to lie substantially parallel to the machine direction, fluid flow in the machine direction is also promoted, which enhances the overall useful absorbency of the article. However, by thus positioning the capillary channel fibers, fluid flow in the cross direction is controlled, thereby minimizing, or even entirely avoiding, leakage of fluid around the lateral edges of the article. Thus, unlike absorbent articles of the prior art which move fluids in an undirected manner in the x, y and z directions by means of fibrous batts which comprise inter-fiber capillary voids, the intra-fiber capillary channels of the fibers provide desirable fluid directionality.

Briefly stated, capillary channel fibers comprise, for example, spinnable polymers (e.g., polyester) formed into thin fibers having external "walls" which define capillary channels along the length of the fiber. Conveniently, the polymers are melt-extrudable. Such walls typically have "H"-shaped, "U"-shaped, " "-shaped or "V"-shaped cross-sections, or repeating multiples or branched structures containing such cross-sections.

While the capillary channel fibers employed herein are typically noncellulosic and are conveniently of the polyester type, it will be appreciated that other types of fiber-forming polymers can be used in their preparation. For example, polyalkenes, polyamides, polylactates, poly-dioxanones, and the like, can be used. Since the objective herein is to have the capillary channel fibers direct, rather than absorb, body fluids, it is preferred that the fibers have minimal, or substantially, no, fluid-imbibing (i.e., water-based body fluids) properties. It will be readily appreciated that, if the fibers themselves absorb fluids and swell, the capillary channels could be choked-off. Thus, cellulose derivatives, for example cellulose propionate, cellulose acetate, and the like, also may be used, if desired, only with due regard for the foregoing considerations.

More specifically, such capillary channel fibers can be produced from various polymers, especially polyethylene terephthalate, which have a denier per filament in the range of from about 10 to about 22, and such fibers are soft and pliable, especially when curled or gathered to impart some degree of loft and resilience. Typical fibers will have walls depths of about 48 microns, and a width-between-walls of about 37 microns. The walls, themselves, are typically 3–15 microns thick.

In a preferred mode, the capillary channel fibers herein are curled (or otherwise gathered). As is known in the fiber art, fiber curling can be achieved by selectively heat quenching the fibers as they come from their forming die by heating one side of the fibers a bit more than the other side (or, conversely, by cooling one side more quickly than the other). Alternatively, fibers made from synthetic polymers such as polyesters can be curled by stretching, followed by relaxation, or by passing the fiber under tension around a sharp edge, followed by relaxation. In another alternative, the fibers (especially multiple branched fibers) can be "gathered" or "carded" in what amounts to curled fibers by mechanical processes, e.g., in a stuffer box. However, the preferred "nonlinear" or curled capillary channel fiber should not be kinked, since kinking can cause points of restriction in the channels, which would impede fluid flow. Some capillary channel fibers can also be curled by immersion in methanol. In a preferred mode, the fibers are substantially helical. In any event, whether curled or mechanically gathered into what amount to curls, it is convenient to speak of the capillary channel fibers optionally used herein as being substantially "curled".

There is a substantial advantage to employing nonlinear capillary channels. It is highly preferred that small portions, or "tufts", of the capillary channel fibers actually protrude into at least some of the topsheet orifices of the articles herein. As can be imagined, these protrusions are easier to effect when a high loft capillary channel pad is prepared using curled capillary channel fibers. Even by chance, there is a greater likelihood that a number of ends and/or curls in the capillary channel fibers will find their way into the orifices of the topsheet material than if substantially linear capillary channels were to be employed.

The preferred amplitude of the curls is in the range of about 0.1 mm to about 3 mm, and, typically, the frequency of the curls is from about 0.5 per cm of fiber to about 5 per cm of fiber. Stated otherwise, an average capillary channel fiber having a straight-line length of about 2 cm is curled or gathered to provide optimal fibers having a length of from about 0.5 cm to about 1.5 cm.

The capillary channel fibers are preferably spontaneously wettable, and are typically hydrophilized, e.g., by the surface application of surfactants such as PEGOSPERSE or VOLPO-3 ethoxylated oleyl alcohol, from Croda, Inc., New York, N.Y., or any other convenient means. Whatever the means, the overall objective is to secure capillary channel fibers for use herein which are spontaneously wettable by the fluids they are intended to transport.

Having thus considered the type of capillary channel fibers employed herein and their individual fiber morphology, the formulator of articles prepared in the manner of this invention will be concerned in the formation of such fibers into absorbent articles. In general, the formulator will be laying-down a bundle of such fibers in the article. In one mode, the fibers can be blown onto, for example, an absorbent core made from cellulosic fibers. In a more preferred mode, multiple capillary channel fibers of the foregoing are formed into a batt or pad, said pad comprising a network of multiple capillary channel fibers. Such multifiber pads will typically have a caliper in the range from about 0.1 in. (0.254 cm) to about 0.7 in. (1.78 cm), preferably from about 0.1 in (0.254 cm) to about 0.4 in. (1.02 cm) for use in sanitary napkins; preferably from about 0.05 in. (0.127 cm) to about 0.15 in. (0.38 cm) for use in pantiliners; and preferably from about 0.1 in. (0.254 cm) to about 0.5 in. (1.27 cm) for use in infant diapers or adult incontinence garments. For use in disposable absorbent articles, such pads will typically have from about 0.003 g to about 0.016 g of fiber per 1 cm$^2$ surface area, and will have from about 0.003 g to about 0.03 g capillary channel fiber per 1 cm$^3$ volume (measured in the uncompressed state). The amounts of fiber per unit area and per unit volume for pantiliners, diapers and adult incontinence garments can be calculated based on the differences in caliper, noted hereinabove.

Preferably, the denier and strength of the capillary channel fibers will be chosen such that the pad of fibers herein will have a ratio of wet:dry caliper of at least about 80%, more preferably at least about 90%. This ensures that the pad will retain its soft and form-fitting qualities even in use.

Stated otherwise, for a typical sanitary napkin, approximately 1.5 g of curled capillary channel fibers of the type described herein will provide a rectangular pad having a surface area of about 160 cm$^2$ which is suitable for use as what might be termed a "secondary topsheet", underlying the initial fluid-receiving topsheet of the type disclosed herein, and overlaying the absorbent core of this invention.

An important consideration in the manufacture of the articles is to ensure close and sustained contact between the topsheet material and the layer of capillary channel fibers. Such close and sustained contact at the interface of the fiber layer and the topsheet maximizes the fluid acceptance and fluid distribution properties of the finished articles.

In a preferred mode, close contact between the topsheet and the layer of capillary channel fibers is achieved by means of adhesive bonding. It will be appreciated that using excessive amounts of adhesive can cause the articles to undesirably stick to the body of the user, and it will also be appreciated that using excessive amounts of adhesive could undesirably clog capillary channels in the fibers, thereby diminishing their effectiveness. Accordingly, "noninterfering" amounts of the adhesive are used. The adhesive should be nonirritating to the skin and otherwise toxicologically-acceptable for use in close contact with delicate body tissues. The adhesive should maintain its bonding properties when moisture is not present, i.e., when the article is being manufactured, and, most preferably, when moisture is present, i.e., when the article is being used.

In one embodiment, the articles herein are prepared in such fashion that at least some of the capillary channel fibers protrude into at least some (preferably at least about 30%, more preferably, at least about 50%) of the openings in that portion of the topsheet which overlays the capillary channel fibers. In yet another mode, at least some of the capillary channel fibers can be needle-punched or otherwise caused to protrude through at least some (preferably at least about 30%, more preferably, at least about 50%) of the openings in that portion of the topsheet which overlays the capillary channel fibers. In this latter instance, the capillary channel fibers will typically protrude through the topsheet for distances of from about 0.1 mm to about 3 cm. This provides for very active uptake of fluid through the topsheet and into the internal region of the absorbent articles provided herein.

The adhesive should bond both to the material used to manufacture the topsheet and to the material used to manufacture the capillary channel fibers. If the topsheet or the fibers are surface-treated, e.g., in a hydrophiliza-tion process, the nature of the surface treatment will have to be considered when selecting the adhesive.

Typical adhesives useful herein include materials selected from latex adhesives and hot melt adhesives. Fortunately, a great variety of such adhesives are well-known in the art, and by giving appropriate attention to the factors mentioned above, the manufacturer can select an appropriate adhesive for any set of circumstances. In order to sustain good contact when the article is in use, i.e., becomes moistened by body fluids, it is preferred that the adhesive be insoluble in body fluids.

While the adhesive can be laid down in a random pattern, it is most preferred that a spiral, or multiple spiral, pattern, be used. In a preferred mode, the lines of adhesive are applied in the spiral or multispiral pattern using a 0.2 mm nozzle, but application using nozzles at least as large as 0.6 mm is satisfactory.

The selection of adhesive can vary with the needs of the formulator, but the following points are instructive. Experience has shown that, in general, latex adhesives tend to be somewhat less satisfactory than hot melt adhesives. Adhesives available from Findley Adhesives, Inc., especially hot melt adhesive 4031, but also, almost uniquely, latex 8085, are useful herein. (Note: Findley H-4031-01 is hydrophobic, which may account for its good performance properties. By contrast, latex H-8082-05 is hydrophilic and may undesirably separate when wetted under in-use conditions.) A variety of hydrophilic finishes can be present on the capillary channel fibers, and the type of adhesive can vary somewhat, depending on the finish used, and its usage level. As noted, the objective is to ensure good contact between the topsheet and the layer of capillary channel fibers at all times, thus maximizing fluid acceptance and partitioning properties. With the Eastman capillary channel fibers such as SW195, Eastman's finish LK 5570 (49% PEG 400 monolaurate/49% PEG 600 monolaurate/2% 4-cetyl-4-ethylmorpholinium ethosulfate [antistat]) works best with Findley adhesive 4031 at high, medium and low (0.78–0.87; 0.38–0.57; 0.28–0.33 wt. percent of fiber) finish levels. Typically, about 0.07 g, 0.08 g or 0.05 g, respectively, depending on high, medium or low finish level, of Findley 4031 gives excellent adhesion.

Other finishes herein include Eastman's LK 5483 (70% PM [PEG 600 monolaurate, polyoxylaurate (13.64) monolaurate]/30% potassium lauryl phosphate), Eastman's LK 5563 (45% PEG 400 monolaurate/45% PEG 600 monolaurate/10% 4-cetyl-4-ethylmor-pholinium ethosulfate) as well as the polymer available as MILEASE T, which is well-known in the detergency arts (see, for example, U.S. Pat. No. 4,132,680) as a fiber-coating ethylene terephthalate/polyethyleneglycol terephthalate soil release polymer, and which is available from ICI Americas.

The amounts of adhesive employed will vary, but typically range from about 0.05 g for a 2 in.×5 in. spiral pattern to about 0.07 g for a 2 in.×7 in. spiral pattern, using a hot melt adhesive. For a latex adhesive, from about 0.1 g to about 0.15 g for a 2 in.×5 in. pattern will suffice. For the spot pattern, about 0.05 g is used in an area of ca. 2 in.×5 in.

Close contact between the topsheet and the underlying layer of capillary channel fibers can be further improved by applying pressure during the gluing process and/or by "combing" the uppermost capillary channel fibers in the layer to provide individual fiber protrusions which give better contact with the adhesive. Alternatively, some proportion of the capillary channel fibers can be driven into the absorbent core of this invention by processes such as needle punching, and the like. This provides an additional route for fluid flow from the capillary channel fiber layer and into the absorbent core.

EXAMPLE XI

A lightweight pantiliner suitable for use between menstrual periods comprises a one gram layer of SW173 capillary channel fibers overlaying a substantially rectangular pad having a surface area of about 117 $cm^2$ and containing the sheet/scrim of Example VI as the absorbent core. The capillary channel fibers are laid down substantially parallel to the long axis of the core. The sheet/scrim plus layer of capillary channel fibers is interposed between the formed-film topsheet of U.S. Pat. No. 4,463,045 and a flexible polyethylene backsheet. Adhesive bonding of the capillary channel fibers to the topsheet is as disclosed hereinabove. The pantiliner functions to absorb vaginal discharges without the need for absorbent gelling materials.

EXAMPLE XII

A catamenial product in the form of a sanitary napkin having two flaps extending outward from its absorbent core is prepared, per the design of U.S. Pat. No. 4,687,478, Van Tilburg, Aug. 18, 1987. The absorbent core comprises a sheet/scrim having a Basis Weight of about 150 pounds, per Example VII herein. A 1.5 g layer of curled SW173 fibers overlays the absorbent core, with the fibers parallel to the long axis of the core. Assembly generally follows the procedure of Example X, herein. The nonglossy sheet of U.S. Pat. No. 4,463,045 is used as the topsheet.

EXAMPLE XIII

The sanitary napkin of Example XII is modified by needle-punching the layer of capillary channel fibers to cause a substantial number of said fibers to partially protrude downward into the absorbent core. This provides additional fluid movement in the Z-direction, i.e., out of the layer of capillary channel fibers and into the absorbent core. Alternatively, the upper layer of the absorbent core is combed or roughed such that fibers from the core extend upward into the layer of capillary channel fibers.

EXAMPLE XIV

The sanitary napkin of Example XII is modified by replacing its formed-film topsheet with a fibrous topsheet according to U.S. Pat. No. 4,636,419 or EPO 215,417, respectively.

In an alternate mode, the scrim used to support and strengthen the absorbent core comprising the refined fibers can comprise capillary channel fibers. Typically, such scrims will comprise about 80% by weight of the capillary channel fibers and about 20% by weight of a fiber whose melting point is below that of the capillary channel fibers. KODEL fibers are suitable, for example. The scrim is prepared in standard fashion by heating to partially melt the lower-melting fibers, which, on cooling, bond the scrim together.

As noted, the layer of refined absorbent fibers is laid-down on the scrim. The resulting structure is then positioned such that the scrim is in fluid-communicating contact with the topsheet of the finished absorbent article.

Having thus described the invention herein in great detail, some additional points are included for consideration by the formulator. It will be appreciated that when capillary channel fibers are optionally used as a scrim onto which is wet-laid an absorbent fibrous core, some of the surfactant on the surface of the capillary channel fibers can be rinsed away. This can be readily replaced by application of additional surfactant, e.g., PEGOSPERSE.

It will be further appreciated that the in-use integrity of absorbent structures comprising the refined, curled fibers disclosed above can be further enhanced by various means. For example, ultrasonic or heat bonding can be used, especially in conjunction with the use of 10–15% by weight of thermoplastic fiber (e.g., KODEL 410 polyester) admixed with the refined fibers. In yet another method, various spot-bonding means can be employed to affix the backsheet to the core, especially over those areas to which the panty-fastening adhesive is applied.

Finally, it is to be appreciated that the preferred articles herein can employ slitted or partially slitted absorbent cores, together with curled capillary channel fibers and other extensible components which, together, provide a degree of extensibility (on the order of 15%–40%) to the article. This extensibility provides better in-use fit, comfort and decreased staining when the articles are affixed to the wearer's undergarments.

In still another mode, the central portion of the layer of capillary channel fibers can be gathered into a small "loop" or "tuft". This loop or tuft thus extends upward from the layer of capillary channel fibers to firmly contact the topsheet. Moreover, the loop or tuft is positioned centrally in the overall article, such that it can provide rapid acquisition and transport of fluid into the remaining portion of the layer of capillary channel fibers, and thence into the fluid storage layer of the article. Advantageously, such "loop" or "tuft" not only concentrates capillary channel fibers at the point where fluid impinges onto the article, but also orients the capillary channel fibers which comprise the loop or tuft substantially in the upward z-direction, thus enhancing fluid movement in the downward z-direction of the article. The following Example illustrates an absorbent article having a substantially central, z-directional tuft of capillary channel fibers.

EXAMPLE XV

A layer of capillary channel fibers of the type disclosed herein (6-inch length) is gathered in its center to provide a slightly raised oval "tuft" having the approximate dimensions: 2–3 inches (x-direction); 1.5 inches (y-direction at widest point); and 5 mm–10 mm (z-direction). The tufted bundle of fibers can be held in its tufted configuration by any convenient means. Typically, the tuft is passed through a confining slit in a sheet of paper or hydrophilic polymer. Using the procedures disclosed herein, the tufted bundle of fibers is assembled into an absorbent article with the tuft residing approximately at the center of the overlying topsheet and with the tuft in close contact with the topsheet, as explained hereinabove. In use as a sanitary napkin, the article is positioned (e.g., intralabially) to maximize fluid uptake by the tuft. In an alternate mode, the ends of the looped fibers in the tuft are cut to provide a fleece-like, z-directional bundle of open-ended capillary channel fibers. In still another embodiment, the layer of capillary channel fibers comprising the base of the tuft is positioned wholly or partly within the absorbent core of the article, rather than atop the core. In this latter embodiment, the core can comprise two tissues of the refined fibers herein, having an intermediate layer of absorbent gelling material (AGM). The layer of capillary channel fibers at the base of the tuft can be slipped into the AGM layer.

The capillary channel fibers can also be conveniently formed into a stable sheet for ease-of-manufacture into absorbent articles by means of various bonding processes. For example, about 20%–30% by weight of polyester thermoplastic fibers (e.g., KODEL 410) can be commingled with the capillary channel fibers and the resulting fibrous sheet subjected to direct thermal or through-air heating.

The refined curled cellulosic fibers can be conveniently formed into a stable sheet for ease-of-manufacture into absorbent articles by means of various bonding processes. For example, about 7%–15% by weight of polyester thermoplastic fibers (e.g., KODEL 410) can be commingled with the refined curled cellulosic fibers and the resulting fibrous sheet subjected to through-air heating or ultrasonic bonding.

Incorporation of the additional thermoplastic fibers into the capillary channel fiber layer or into the absorbent core layer, or both, offers advantages in addition to the sheet stability noted above. In particular, having the thermoplastic fibers present in the core, or in the capillary channel fiber layer, or both, allows the manufacturer to provide a seal at the periphery (at least in the crotch region) of, for example, a sanitary napkin or pantiliner, said seal providing a means whereby fluid overflow around the edges of the article is impeded, or stopped altogether.

More particularly, an article of the foregoing type can be prepared by laying-down a sheet of the refined curled cellulosic fibers containing the thermoplastic fibers onto a standard plastic backing sheet. At a position about 0.25 in. inboard from the outer edge of the sheet, a substantially continuous ultrasonic bond approximately 0.125 in. wide is formed around the periphery of the core. This not only forms the fluid-impeding seal, but also bonds the core to the backsheet.

In an alternate mode, the thermoplastic topsheet, the core containing the thermoplastic fibers and the backsheet can all be bonded together at or near the periphery by means of ultrasonic bonding. In still another mode, the layer of capillary channel fibers containing the admixed thermoplastic fibers can likewise be bonded to the core (and also to the topsheet, if desired). In still another mode, the presence of thermoplastic fibers in the core and/or in the layer of capillary fibers allows for spot bonding at various points across the article, thereby providing additional integrity when the article becomes wet.

While it will be appreciated by those familiar with the physics of fluid transport that the articles herein conveniently make use of the differences in spacings between topsheet, capillary channel fibers and core to establish a pressure gradient to draw fluids in the z-direction, other means can be employed to establish such z-direction fluid-flow gradient. For example, if the holes or spacings in the topsheet are smaller than the width of the capillary channel fibers (and such intra-fiber channel widths as wide as 90 microns may be useful for transporting relatively thick fluids such as menses), then the desired pressure gradient can be established, for example, by selecting a topsheet which is more hydrophobic than the capillary channel fibers.

While the foregoing illustrates the use of the refined fibers herein in conventional pad-type catamenials, the fibers also find other uses. The slurry of the refined fibers herein is quite "workable" and, as noted, is readily dewatered. Thus, the slurry can be passed into 3-dimensional shaped molds which can be designed to afford absorbent catamenial devices of the convex intralabial, or concave external, or pessary types. Indeed, the slurries can thus be fashioned into any desired, anatomical shape (the literature is replete with various designs), including shapes suitable for internal vaginal usage.

What is claimed is:

1. An absorbent article comprising:
   (a) a fluid-permeable topsheet;
   (b) a fluid-impermeable backsheet joined to said topsheet; and
   (c) an absorbent core positioned between said topsheet and said backsheet, said absorbent core comprising a wet-laid sheet of substantially uniformly distributed unrefined individualized curled cellulosic fibers having an average length from about 1.6 mm to about 7 mm and at least about 30% of refined individualized curled cellulosic fibers having an average length from about 0.25 mm to about 1.5 mm.

2. The absorbent article according to claim 1 wherein said absorbent core has an average of from about 0.1 g to about 0.15 g of said refined fibers per cubic centimeter.

3. The absorbent article according to claim 1 wherein said absorbent core has from about 50% to about 90% of refined individualized curled cellulosic fibers.

4. The absorbent article according to claim 3 wherein said absorbent core has an average thickness of from about 0.3 mm to about 2.4 mm.

5. An absorbent article comprising:
   (a) a fluid-permeable topsheet;
   (b) a fluid-impermeable backsheet joined to said topsheet; and
   (c) an absorbent core positioned between said topsheet and said backsheet, said absorbent core comprising a nonwoven onto which is cohesively wet-laid a layer of substantially uniformly distributed unrefined individualized curled cellulosic fibers having an average length from about 1.6 mm to about 7 mm and at least about 30% of refined individualized curled cellulosic fibers having an average length from about 0.25 mm to about 1.5 mm.

6. The absorbent article according to claim 5 wherein said absorbent core has from about 50% to about 90% of refined individualized curled cellulosic fibers.

7. The absorbent article according to claim 6 wherein said absorbent core has an average of about 0.1 g to about 0.15 g of said refined fibers per cubic centimeter.

8. The absorbent article according to claim 7 wherein said absorbent core has an average thickness of from about 0.3 mm to about 2.4 mm.

9. An absorbent article having a long axis and a short axis, said absorbent article comprising:
   (a) a fluid-permeable topsheet;
   (b) a fluid-impermeable backsheet joined to said topsheet; and
   (c) an absorbent core positioned between said topsheet and said backsheet, said absorbent core comprising a fluid-directing batt of fibers having external capillary channels, and wherein a layer of substantially uniformly distributed unrefined individualized curled cellulosic fibers having an average length from about 1.6 mm to about 7 mm and at least about 30% of refined individualized curled cellulosic fibers having an average length from about 0.25 mm to about 1.5 mm are cohesively wet-laid onto said batt.

10. The absorbent article according to claim 9 wherein the batt of capillary channel fibers is in close, fluid-transporting contact with said topsheet.

11. The absorbent article according to claim 9 wherein said absorbent core has from about 50% to about 90% of refined individualized curled cellulosic fibers.

12. The absorbent article according to claim 11 wherein said absorbent core has an average of from about 0.1 g to about 0.15 g of said refined fibers per cubic centimeter.

13. The absorbent article according to claim 12 wherein said absorbent core has an average thickness of from about 0.3 mm to about 2.4 mm.

14. An absorbent article having a long axis and a short axis, said absorbent article comprising:
 (a) a fluid-permeable topsheet;
 (b) a fluid-impermeable backsheet joined to said topsheet; and
 (c) an absorbent core positioned between said topsheet and said backsheet, said absorbent core comprising a fluid-directing batt of fibers having external capillary channels, wherein at least 50% of the fibers having capillary channels are positioned such that their capillary channels lie substantially parallel to the long axis of said absorbent article, and wherein a layer of substantially uniformly distributed unrefined individualized curled cellulosic fibers having an average length from about 1.6 mm to about 7 mm and at least about 50% to about 90% of refined individualized curled cellulosic fibers having an average length from about 0.25 mm to about 1.5 mm are cohesively wet-laid onto said batt, said layer having an average of from about 0.1 g to about 0.15 g of said refined fibers per cubic centimeter, and an average thickness of from about 0.3 mm to about 2.4 mm.

15. An absorbent article having a long axis and a short axis, said absorbent article comprising:
 (a) a fluid-permeable topsheet;
 (b) a fluid-impermeable backsheet joined to said topsheet; and
 (c) an absorbent core positioned between said topsheet and said backsheet, said absorbent core comprising a fluid-directing batt of fibers having external capillary channels, wherein said absorbent core has at least about 50% of the capillary channel fibers in its batt positioned such that the capillary channels lie substantially parallel to the long axis of said absorbent article, said batt of capillary channel fibers is in close, fluid-transporting contact with said topsheet, and wherein a layer of substantially uniformly distributed unrefined individualized curled cellulosic fibers having an average length from 1.6 mm to about 7 mm and at least about 30% of refined individualized curled cellulosic fibers having an average length from about 0.25 mm to about 1.5 mm are cohesively wet-laid onto said batt.

16. An absorbent article having a long axis and a short axis, said absorbent article comprising:
 (a) a fluid-permeable topsheet;
 (b) a fluid-impermeable backsheet joined to said topsheet; and
 (c) an absorbent core positioned between said topsheet and said backsheet, said absorbent core comprising a fluid-directing batt of fibers having external capillary channels wherein at least about 50% of said fibers having external capillary channels are positioned such that their capillary channels lie substantially parallel to the long axis of said absorbent article and wherein a layer of substantially uniformly distributed unrefined individualized curled cellulosic fibers having an average length from about 1.6 mm to about 7 mm and at least about 30% of refined individualized curled cellulosic fibers having an average length from about 0.25 mm to about 1.5 mm are cohesively wet-laid onto said batt.

17. The absorbent article according to claim 16, wherein the batt of fibers having external capillary channels is in close, fluid-transporting contact with said topsheet.

18. The absorbent article according to claim 16 wherein said absorbent core has from about 50% to about 90% of refined individualized curled cellulosic fibers.

19. The absorbent article according to claim 18 wherein said absorbent core has an average from about 0.1 g to about 0.15 g of said refined fibers per cubic centimeter of said wet-laid layer.

20. The absorbent article according to claim 19 wherein said absorbent core has an average thickness of from about 0.3 mm to about 2.4 mm.

* * * * *